(12) United States Patent
Simaan et al.

(10) Patent No.: US 9,549,720 B2
(45) Date of Patent: Jan. 24, 2017

(54) ROBOTIC DEVICE FOR ESTABLISHING ACCESS CHANNEL

(71) Applicant: Vanderbilt University, Nashville, TN (US)

(72) Inventors: Nabil Simaan, Nashville, TN (US); Andrea Bajo, Fort Lauderdale, FL (US)

(73) Assignee: Vanderbilt University, Nashville, TN (US)

( * ) Notice: Subject to any disclaimer, the term of this patent is extended or adjusted under 35 U.S.C. 154(b) by 236 days.

(21) Appl. No.: 14/394,245

(22) PCT Filed: Apr. 19, 2013

(86) PCT No.: PCT/US2013/037353
§ 371 (c)(1),
(2) Date: Oct. 13, 2014

(87) PCT Pub. No.: WO2013/158983
PCT Pub. Date: Oct. 24, 2013

(65) Prior Publication Data
US 2015/0119900 A1    Apr. 30, 2015

Related U.S. Application Data

(60) Provisional application No. 61/636,506, filed on Apr. 20, 2012.

(51) Int. Cl.
*A61M 25/01* (2006.01)
*A61B 17/02* (2006.01)
(Continued)

(52) U.S. Cl.
CPC ....... *A61B 17/0218* (2013.01); *A61B 1/00006* (2013.01); *A61B 1/0055* (2013.01);
(Continued)

(58) Field of Classification Search
CPC ... A61B 1/00; A61B 1/00064; A61B 1/00071; A61B 1/00078; A61B 1/00082; A61B 1/00147; A61B 1/00154; A61B 1/0055; A61B 1/0057; A61B 1/008; A61B 1/01; A61B 17/0218; A61B 2034/301; A61B 2034/302; A61B 2034/303; A61B 2034/306; A61B 34/30; A61B 34/70; A61B 34/71; A61B 34/76; A61M 2025/015; A61M 25/0102; A61M 25/0105; A61M 25/0133; A61M 25/0144; A61M 25/0147
See application file for complete search history.

(56) References Cited

U.S. PATENT DOCUMENTS 2,988,237 A    6/1961 Devol, Jr.
3,580,099 A    5/1971 Mosher
(Continued)

FOREIGN PATENT DOCUMENTS

EP    2335558    6/2011
WO    2005009482    2/2005
(Continued)

OTHER PUBLICATIONS

W. Wei, K. Xu. and N. Simaan, "A compact Two-armed Slave Manipulator for Minimally Invasive Surgery of the Throat," in IEEE RAS/EMBS International Conference on Biomedical Robotics and Biomechatronics, 2006, pp. 769-774.
(Continued)

*Primary Examiner* — Ryan J Severson
(74) *Attorney, Agent, or Firm* — Michael Best & Friedrich LLP

(57) ABSTRACT

A device for establishing an access channel to a target location is presented. The device includes a plurality of cylindrical segments. A plurality of backbones each extends through a backbone channel of each segment to join the
(Continued)

plurality of segments together. When joined together, the central bore of each of the plurality of cylindrical segments align to form an access channel. A distal segment is fixedly attached to each of the plurality of backbones such that an orientation of the distal segment can be adjusted by linear movement of one or more of the plurality of backbones through the plurality of cylindrical segments. Furthermore, when linear movement of the plurality of backbones is restricted, the shape of the access channel can be adjusted by external forces while maintaining the orientation of the distal segment.

20 Claims, 6 Drawing Sheets

(51) Int. Cl.
 A61B 1/00 (2006.01)
 A61B 1/005 (2006.01)
 A61M 25/10 (2013.01)
(52) U.S. Cl.
 CPC ...... *A61B 1/00147* (2013.01); *A61B 1/00154* (2013.01); *A61B 34/30* (2016.02); *A61M 25/0144* (2013.01); *A61M 25/10* (2013.01); *A61B 1/00082* (2013.01); *A61B 2034/303* (2016.02); *A61B 2034/306* (2016.02)

(56) References Cited

U.S. PATENT DOCUMENTS

| | | | |
|---|---|---|---|
| 4,744,264 A | 5/1988 | Milenkovic |
| 4,795,296 A | 1/1989 | Jau |
| 4,802,461 A | 2/1989 | Cho |
| 5,046,375 A | 9/1991 | Salisbury, Jr. et al. |
| 5,231,989 A | 8/1993 | Middleman et al. |
| 5,337,732 A | 8/1994 | Grundfest et al. |
| 5,345,937 A | 9/1994 | Middleman et al. |
| 5,386,741 A | 2/1995 | Rennex |
| 5,397,323 A | 3/1995 | Taylor et al. |
| 5,410,638 A | 4/1995 | Colgate et al. |
| 5,480,406 A | 1/1996 | Nolan et al. |
| 5,662,587 A | 9/1997 | Grundfest et al. |
| 5,749,828 A | 5/1998 | Solomon et al. |
| 6,113,593 A | 9/2000 | Tu et al. |
| 6,197,017 B1 | 3/2001 | Brock et al. |
| 6,309,346 B1 | 10/2001 | Farhadi |
| 6,554,844 B2 | 4/2003 | Lee et al. |
| 6,669,711 B1 | 12/2003 | Noda |
| 6,676,684 B1 | 1/2004 | Morley et al. |
| 6,692,485 B1 | 2/2004 | Brock et al. |
| 6,817,974 B2 | 11/2004 | Cooper et al. |
| 6,837,892 B2 | 1/2005 | Shoham |
| 6,843,793 B2 | 1/2005 | Brock et al. |
| 6,858,005 B2 | 2/2005 | Ohline et al. |
| 6,860,878 B2 | 3/2005 | Brock |
| 6,949,106 B2 | 9/2005 | Brock et al. |
| 7,021,173 B2 | 4/2006 | Stoianovici et al. |
| 7,099,745 B2 | 8/2006 | Ebert |
| 7,214,230 B2 | 5/2007 | Brock et al. |
| 7,235,089 B1 | 6/2007 | McGuckin, Jr. |
| 7,316,681 B2 | 1/2008 | Madhani et al. |
| 7,391,173 B2 | 6/2008 | Schena |
| 7,682,319 B2 | 3/2010 | Martin et al. |
| 7,699,835 B2 | 4/2010 | Lee et al. |
| 7,787,681 B2 | 8/2010 | Zhang et al. |
| 7,822,249 B2 | 10/2010 | Garty et al. |
| 7,837,615 B2 | 11/2010 | Le et al. |
| 7,854,738 B2 | 12/2010 | Lee et al. |
| 7,887,549 B2 | 2/2011 | Wenderow et al. |
| 7,959,557 B2 | 6/2011 | Weitzner et al. |
| 8,025,635 B2 | 9/2011 | Eaton et al. |
| 8,088,101 B2 | 1/2012 | Chang et al. |
| 8,114,062 B2 | 2/2012 | Muni et al. |
| 8,116,886 B2 | 2/2012 | Simaan et al. |
| 8,172,828 B2 | 5/2012 | Chang et al. |
| 8,303,576 B2 | 11/2012 | Brock |
| 8,311,626 B2 | 11/2012 | Hlavka et al. |
| 8,337,521 B2 | 12/2012 | Cooper et al. |
| 8,343,141 B2 | 1/2013 | Madhani et al. |
| 8,365,633 B2 | 2/2013 | Simaan et al. |
| 8,372,019 B2 | 2/2013 | Goldenberg et al. |
| 8,377,077 B2 | 2/2013 | Reis |
| 8,409,234 B2 | 4/2013 | Stahler et al. |
| 8,414,505 B1 | 4/2013 | Weitzner et al. |
| 8,414,598 B2 | 4/2013 | Brock et al. |
| 8,444,549 B2 | 5/2013 | Viola et al. |
| 8,460,236 B2 | 6/2013 | Roelle et al. |
| 8,480,618 B2 | 7/2013 | Wenderow et al. |
| 8,486,053 B2 | 7/2013 | Niemeyer |
| 8,498,691 B2 | 7/2013 | Moll et al. |
| 8,504,201 B2 | 8/2013 | Moll et al. |
| 8,545,551 B2 | 10/2013 | Loulmet |
| 8,551,115 B2 | 10/2013 | Steger et al. |
| 8,585,731 B2 | 11/2013 | Abbate et al. |
| 8,864,757 B2 | 10/2014 | Klimovitch et al. |
| 2002/0120252 A1 | 8/2002 | Brock et al. |
| 2003/0120305 A1 | 6/2003 | Jud et al. |
| 2004/0116906 A1 | 6/2004 | Lipow |
| 2004/0176751 A1 | 9/2004 | Weitzner et al. |
| 2005/0043718 A1 | 2/2005 | Madhani et al. |
| 2005/0054900 A1 | 3/2005 | Mawn et al. |
| 2005/0059960 A1 | 3/2005 | Simaan et al. |
| 2005/0228440 A1 | 10/2005 | Brock et al. |
| 2006/0036182 A1 | 2/2006 | Daniels et al. |
| 2006/0047302 A1 | 3/2006 | Ortiz et al. |
| 2006/0058861 A1 | 3/2006 | Gibson et al. |
| 2006/0156851 A1 | 7/2006 | acobsen et al. |
| 2006/0241414 A1 | 10/2006 | Nowlin et al. |
| 2006/0258938 A1 | 11/2006 | Hoffman et al. |
| 2007/0197939 A1 | 8/2007 | Wallace et al. |
| 2007/0225787 A1 | 9/2007 | Simaan et al. |
| 2008/0033240 A1 | 2/2008 | Hoffman et al. |
| 2008/0065108 A1 | 3/2008 | Diolaiti |
| 2008/0071288 A1 | 3/2008 | Larkin et al. |
| 2008/0114492 A1 | 5/2008 | Miegel et al. |
| 2008/0179301 A1 | 7/2008 | Garty et al. |
| 2008/0181473 A1 | 7/2008 | Garty et al. |
| 2008/0188800 A1 | 8/2008 | Bencini et al. |
| 2008/0243063 A1 | 10/2008 | Camarillo |
| 2008/0243064 A1 | 10/2008 | Stahler et al. |
| 2008/0243106 A1 | 10/2008 | Coe et al. |
| 2008/0245173 A1 | 10/2008 | Schwerin et al. |
| 2008/0249536 A1 | 10/2008 | Stahler et al. |
| 2008/0262513 A1 | 10/2008 | Stahler et al. |
| 2008/0302200 A1 | 12/2008 | Tobey |
| 2009/0054222 A1 | 2/2009 | Zhang et al. |
| 2009/0076476 A1 | 3/2009 | Barbagli et al. |
| 2009/0076521 A1 | 3/2009 | Hansen |
| 2009/0088774 A1 | 4/2009 | Swarup et al. |
| 2009/0171151 A1 | 7/2009 | Choset et al. |
| 2009/0216083 A1 | 8/2009 | Durant et al. |
| 2009/0275818 A1 | 11/2009 | Rau et al. |
| 2009/0275857 A1 | 11/2009 | Cabiri et al. |
| 2010/0010504 A1 | 1/2010 | Simaan et al. |
| 2010/0011900 A1 | 1/2010 | Burbank |
| 2010/0030377 A1 | 2/2010 | Unsworth |
| 2010/0069719 A1 | 3/2010 | Wehrheim |
| 2010/0076269 A1 | 3/2010 | Makower et al. |
| 2010/0079308 A1 | 4/2010 | Fabre et al. |
| 2010/0099951 A1 | 4/2010 | Laby et al. |
| 2010/0125165 A1 | 5/2010 | Torii et al. |
| 2010/0152899 A1 | 6/2010 | Chang et al. |
| 2010/0256558 A1 | 10/2010 | Olson et al. |
| 2010/0331858 A1 | 12/2010 | Simaan et al. |
| 2011/0015649 A1 | 1/2011 | Anvari et al. |
| 2011/0066160 A1 | 3/2011 | Simaan et al. |
| 2011/0071541 A1 | 3/2011 | Prisco et al. |
| 2011/0071544 A1 | 3/2011 | Steger et al. |
| 2011/0125165 A1 | 5/2011 | Simaan et al. |
| 2011/0184241 A1 | 7/2011 | Zubiagte et al. |
| 2011/0196419 A1 | 8/2011 | Cooper |

(56) References Cited

U.S. PATENT DOCUMENTS

| | | | |
|---|---|---|---|
| 2011/0213346 | A1 | 9/2011 | Morley et al. |
| 2011/0230894 | A1 | 9/2011 | Simaan et al. |
| 2011/0306929 | A1 | 12/2011 | Levesque et al. |
| 2011/0313243 | A1 | 12/2011 | Zubiate et al. |
| 2011/0319910 | A1 | 12/2011 | Roelle et al. |
| 2012/0071822 | A1 | 3/2012 | Romo et al. |
| 2012/0109274 | A1 | 5/2012 | Simaan et al. |
| 2012/0123395 | A1 | 5/2012 | Stoy et al. |
| 2012/0241576 | A1 | 9/2012 | Yu |
| 2012/0253131 | A1 | 10/2012 | Malkowski et al. |
| 2012/0289946 | A1 | 11/2012 | Steger |
| 2013/0012928 | A1 | 1/2013 | Cooper et al. |
| 2013/0023859 | A1 | 1/2013 | Malkowski |
| 2013/0090763 | A1 | 4/2013 | Simaan et al. |
| 2013/0096540 | A1 | 4/2013 | Cooper et al. |
| 2013/0110131 | A1 | 5/2013 | Madhani et al. |
| 2013/0131868 | A1 | 5/2013 | Rucker et al. |
| 2013/0165869 | A1 | 6/2013 | Blumenkranz et al. |
| 2013/0165945 | A9 | 6/2013 | Roelle et al. |
| 2013/0178838 | A1 | 7/2013 | Malkowski |
| 2013/0190741 | A1 | 7/2013 | Moll et al. |
| 2013/0197539 | A1 | 8/2013 | Simaan et al. |
| 2013/0218141 | A1 | 8/2013 | Hinman et al. |
| 2013/0231529 | A1 | 9/2013 | John et al. |
| 2013/0269109 | A1 | 10/2013 | Yu |
| 2013/0274715 | A1 | 10/2013 | Chan et al. |
| 2013/0289581 | A1 | 10/2013 | Yeung et al. |
| 2013/0300537 | A1 | 11/2013 | Bajo et al. |
| 2013/0303945 | A1 | 11/2013 | Blumenkranz et al. |
| 2013/0306112 | A1 | 11/2013 | Blumenkranz |
| 2013/0338433 | A1 | 12/2013 | Goldman et al. |
| 2014/0058406 | A1 | 2/2014 | Tsekos |
| 2014/0330432 | A1 | 11/2014 | Simaan et al. |
| 2015/0073434 | A1 | 3/2015 | Simaan et al. |

FOREIGN PATENT DOCUMENTS

| | | |
|---|---|---|
| WO | 2005112834 | 12/2005 |
| WO | 2008036304 | 3/2008 |
| WO | 2009094670 | 7/2009 |
| WO | 2009097461 | 8/2009 |
| WO | 2009097539 | 8/2009 |
| WO | 2009124287 | 10/2009 |
| WO | 2009140688 | 11/2009 |
| WO | 2010042611 | 4/2010 |
| WO | 2011063511 | 6/2011 |
| WO | 2012015816 | 2/2012 |
| WO | 2012049623 | 4/2012 |
| WO | 2013043804 | 3/2013 |
| WO | 2013158974 | 10/2013 |
| WO | 2013158978 | 10/2013 |
| WO | 2013158983 | 10/2013 |
| WO | 2013166293 | 11/2013 |

OTHER PUBLICATIONS

Wei, W., Goldman, R. E., Simaan, N., Fine, H. & Chang, S (2007). Design and Theoretical Evaluation of Micro-Surgical Manipulators for Orbital Manipulation and Intraocular Dexterity. In 2007 IEEE International Conference on Robotics and Automation, pp. 3389-3395. Roma, Italy.

Wei, W., and Simaan, N. Modeling, Force Sensing, and Control of Flexible Cannulas for Microstent Delivery. Journal of Dynamic Systems, Measurement, and Control 134, 4 (2012), 041004.

Wei, W., Popplewell, C., Fine, H., Chang, S., Simaan, N., "Enabling Technology for Micro-Vascular Stenting in Ophthalmic Surgery," ASME Journal of Medical Devices (JMED), vol. 4, Issue 1, 014503 (6 pages) doi:10.1115/1.4001193, 2010.

A. Bajo and N. Simaan, "Configuration and Joint Feedback for Enhanced Performance of Multi-Segment Continuum Robots," in IEEE International Conference on Robotics and Automation, 2011, pp. 2905-2912.

A. Bajo and N. Simaan, "Finding Lost Wrenches: Using Continuum Robots for Contact Detection and Estimation of Contact Location," 2010 IEEE International Conference on Robotics and Automation (May 3-8, 2010).

A. Bajo, and N. Simaan, Kinematics-Based Detection and Localization of Contacts Along Multisegment Continuum Robots. IEEE Transactions on Robotics 28, 2 (Apr. 2012), 291-302.

R.E. Goldman, A. Bajo, and N. Simaan, Compliant Motion Control for Continuum Robots with Intrinsic Actuation Sensing. In 2011 IEEE International Conference on Robotics and Automation (Shanghai, China, 2011), pp. 1126-1132.

Bajo, A., Dharamsi, L., Netterville, J. L., Garrett, G. C., and Simaan, N (2013). Robotic-Assisted Micro-Surgery of the Throat: the Trans-Nasal Approach. In Accepted for publication in IEEE International Conference on Robotics and Automation (ICRA'2013).

A. Kapoor, M. Li, and R. H. Taylor, "Spatial Motion Constraints for Robot Assisted Suturing using Virtual Fixtures," 2005, vol. 3750, pp. 89-96.

A. Kapoor and R.H. Taylor, A Constrained Optimization Approach to Virtual Fixtures for Multi-Handed Tasks. In IEEE International Conference on Robotics and Automation (Pasadena, CA, 2008), pp. 3401-3406.

Agrawal, V., Peine, W. J., Yao, B., and Choi, S. Control of Cable Actuated Devices using Smooth Backlash Inverse. In 2010 IEEE International Conference on Robotics and Automation (Anchorage, AK, 2010), pp. 1074-1079.

Angeles, J. Automatic Computation of the Screw Parameters of Rigid-Body Motions. Part II: Infinitesimally-Separated Positions. Journal of Dynamic Systems, Measurement, and Control 108, Mar. 1986, 32-38.

Baki, P., Szekely, G., and Kosa, G. Miniature tri-axial force sensor for feedback in minimally invasive surgery. In 2012 4th IEEE RAS & EMBS In-ternational Conference on Biomedical Robotics and Biomechatronics (BioRob) (Roma, Italy, Jun. 2012), IEEE, pp. 805-810.

Bhattacharyya, S. (2011). Motion Planning and Constraint Exploration for Robotics Surgery. Master Thesis, Vanderbilt University, Nashville, TN.

Bhattacharyya, S. & Simaan, N (2013). Characterization of Constraints in Flexible Unknown Environments. In Accepted for publication in IEEE International Conference on Robotics and Automation (ICRA'2013).

Birkfellner, W., Watzinger, F., Wanschitz, F., Ewers, R., and Bergmann, H. Calibration of tracking systems in a surgical environment. IEEE Transactions on Medical Imaging 17, 5 (Oct. 1998), 737-42.

Bokelberg, E. H., Hunt, K. H., and Ridley, P. R. Spatial Motion—I: Points of inflection and the differential geometry of screws. Mechanism and Machine Theory 27, 1 (1992), 1-15.

Burgner, J., Swaney, P. J., Rucker, D. C., Gilbert, H. B., Nill, S. T., Russell III, P. T. R., Weaver, K. D., Iii, R. J. W., Russell, P. T., and Webster, R. J. A Bimanual Teleoperated System for Endonasal Skull Base Surgery. In 2011 IEEE International Conference on In-telligent Robots and Systems (San Francisco, CA, Sep. 2011), IEEE, pp. 2517-2523.

Camarillo, D. B., Carlson, C. R., and Salisbury, J. K. Configuration Tracking for Continuum Manipulators With Coupled Tendon Drive. IEEE Transactions on Robotics 25, 4 (Aug. 2009), 798-808.

Camarillo, D. B., Milne, C. F., Carlson, C. R., Zinn, M. R., and Salisbury, J. K. Mechanics Modeling of Tendon-Driven Continuum Manipulators. IEEE Transaction on Robotics 24, 6 (2008), 1262-1273.

Camarillo, D. B., Loewke, K., Carlson, C. R., and Salisbury, J. K. Vision based 3-D shape sensing of flexible manipulators. In 2008 IEEE International Conference on Robotics and Automation (Pasadena, CA, 2008), pp. 2940-2947.

Cauberg, E. C., de la Rosette, J. J., and de Reijke, T. M. How to improve the effectiveness of transurethral resection in nonmuscle invasive bladder cancer? Current Opinion in Urology 2 19, 5 (2009), 504-510.

(56) References Cited

OTHER PUBLICATIONS

Chan, T. F., and Dubey, R. V. A Weighted Least-Norm Solution Based Scheme for Avoiding Joint Limits for Redundant Joint Manipulators. IEEE Transaction on Robotics and Automation 11, 2 (1995), 286-292.
Chirikjian, G. S., and Burdick, J. W. A Modal Approach to Hyper-Redundant Manipulator Kinematics. IEEE Transaction on Robotics and Au-tomation 10, 3 (1994), 343-354.
Chirikjian, G. S., and Burdick, J. W. An obstacle avoidance algorithm for hyper-redundant manipulators. In Proceedings., IEEE International Conference on Robotics and Automation (1990), IEEE Comput. Soc. Press, pp. 625-631.
Croom, J. M., Rucker, D. C., Romano, J. M., and Webster, R. J. I. Visual Sensing of Continuum Robot Shape Using Self-Organizing Maps. In 2010 IEEE International Conference on Robotics and Automation (Anchorage, AK, 2010), pp. 4591-4596.
De Luca, A., Haddadin, S., and Hirzinger, G. Collision Detection and Safe Reaction with the DLR-III Lightweight Manipulator Arm. In 2006 IEEE/RSJ International Conference on Intelligent Robots and Systems (Beijing, China, 2006), pp. 1623-1630.
De Luca, A., and Manes, C. Modeling of Robots in Contact with a Dynamic Environment. IEEE Transaction on Robotics and Auto-mation 10,4 (1994), 542-548.
Degani, A., Choset, H., Wolf, A., and Zenati, M. A. Highly Articulated Robotic Probe for Minimally Invasive Surgery. In 2006 IEEE Inter-national Conference on Robotics and Automation (Orlando, FL, USA, 2006), pp. 4167-4172.
Dimaio, S. da Vinci and Beyond. In 2010 IEEE International Conference on Robotics and Automation Workshop on Medical Cyber-Physical Systems (Anchorage, AK, 2010).
Ding, J., Goldman, R. E., Xu, K., Allen, P. K., Fowler, D. L., and Simaan, N. Design and Coordination Kinematics of an Insertable Robotic Effectors Platform for Single-Port Access Surgery. IEEE/ASME Transactions on Mechatronics (2012), 1-13.
Dupont, P., Lock, J., Itkowitz, B., and Butler, E. Design and Control of Concentric-Tube Robots. IEEE Transaction on Robotics 26,2 (2010), 209-225.
Eberman, B. S., and Salisbury, J. K. Determination of Manipulator Contact Information from Joint Torque Measurements. In Experimental Robotics I, vol. 139. Springer, 1990, pp. 463-473.
Featherstone, R. Modeling and Control of Contact Between Constrained Rigid Bodies. IEEE Transaction on Robotics and Automation 20, 1 (2004), 82-92.
Featherstone, R., Thiebaut, S. S., and Khatib, O. A General Contact Model for Dynamically-Decoupled Force/Motion Control. In 1999 IEEE International Conference on Robotics and Automation (1999), No. May, pp. 3281-3286.
Fine, H., Wei, W., Simaan, N., "Could Robots Ever Do Retina Surgery? ," Review of Ophthalmology, vol. 17, No. 5, Issue: May 1, 2010.
Fine, H., Wei, W., Chang, S. & Simaan, N (2009). A novel dual-arm dexterous ophthalmic microsurgical robot: applications for retinal vascular cannulation and stent deployment. In American Society of Retinal Specialists, Retina Congress 2009, New York, NY, Sep. 4-Oct. 4.
Garty, G., Randers-Pehrson, G., Simaan, N., Salerno, A., A., D., J., N. et al (2007). Development of an ultrahigh-throughput robotically-based biodosimetry workstation using in-situ assays. In 13th International Congress of Radiation Research, San Francisco, California, Jul. 8-12, 2007.
Ikuta, K., Yamamoto, K., and Sasaki, K. Development of remote micro-surgery robot and new surgical procedure for deep and narrow space. In 2003 IEEE International Conference on Robotics and Automation (Taipei, Taiwan, 2003), vol. 1, IEEE, pp. 1103-1108.
J. Zhang and N. Simaan, "Optimal Design of Under-actuated Steerable Electrode Arrays for Optimal Insertions," ASME Journal on Mechanisms and Robotics, Submitted , 2010.

Goldman, R. E. (2011). Analysis, Algorithms, and Control for Intelligent Surgical Exploration and Intervention. Phd Thesis, Columbia University (graduated with distinction).
Goldman, R. E., Bajo, A., Suh, L., Benson, M. & Simaan, N (2011). Rapidly Deployable Telerobotic Slave for Transurethral Exploration and Intervention. In presented in the 2011 Annual Engineering and Urology Society annual meeting, May 14, Washington, DC.
Goldman, R. E., Bajo, A. & Simaan, N. (2013). Algorithms for Autonomous Exploration and Estimation in Compliant Environments. Robotica, 31(1), 71-88.
Goldman, R. E., Bajo, A., MacLachlan, L. S., Pickens, R., Herrell, S. D. & Simaan, N. (2013). Design and Performance Evaluation of a Minimally Invasive Telerobotic Platform for Transurethral Surveillance and Intervention. IEEE Transactions on Biomedical Engineering, 60(4), 918-925.
Gravagne, I. A., and Walker, I. D. Kinematic Transformations for Remotely-Actuated Planar Continuum Robots. In 2000 IEEE International Conference on Robotics & Automation (San Francisco, 2000), No. April, pp. 19-26.
Guthart, G., and Salisbury, K. The IntuitiveTM Telesurgery System: Overview and Application. In 2000 IEEE International Conference on Robotics and Automation (2000), pp. 618-621.
Haddadin, S., De Luca, A., and Hirzinger, G. Collision Detection and Reaction: A Contribution to Safe Physical Human-Robot Interaction. In 2008 IEEE/RSJ International Conference on Intelligent Robots and Systems (Nice, France, 2008), pp. 3356-3363.
Herrell SD, Kwartowitz DM, Milhoua PM, Galloway RL. Toward Image-Guided Robotic Surgery: System Validation. J Urol. Feb. 2009; 181(2): 783-9 Discussion 789-90. Epub Dec. 16, 2008.
Ho, S. C., Hibberd, R. D., and Davies, B. L. Robot Assisted Knee Surgery. IEEE Engineering in Medicine and Biology Magazine 14,3 (1995), 292-299.
Howell, L. L. Compliant Mechanisms. Wiley-Interscience, 2001.
Ikits, M., Brederson, J. D., Hansen, C. D., and Hollerbach, J. M. An Improved Calibration Framework for Electromagnetic Tracking Devices. In 2001 IEEE Virtual Reality (Yokohama, Japan, 2001), IEEE Comput. Soc, pp. 63-70.
J. Zhang, K. Xu, N. Simaan, and S. Manolidis, "A Pilot Study of Robot-Assisted Cochlear Implant Surgery Using Steerable Electrode Arrays," in International Conference on Medical Image Computing and Computer-Assisted Intervention (MICCAI '06), 2006, pp. 33-40.
J. Zhang, S. Manolidis, T. J. Roland, and N. Simaan, "Path Planning and Workspace Determination for Robot-Assisted Insertion of Steerable Electrode Arrays for Cochlear Implant Surgery," 2008.
J. Zhang, T. J. Roland, S. Manolidis, and N. Simaan, "Optimal Path Planning for Robotic Insertion of Steerable Electrode Arrays in Cochlear Implant Surgery," ASME Journal of Medical Devices, vol. 3, No. 1, 2009.
Zhang, J., Wei, W., Ding. J., Rolant, T.J., Manolidis, S., Simaan, N., "Inroads towards Robot-Assisted Cochlear Implant Surgery using Steerable Electrode Arrays", Otology & Neurology special issue on Cochlear Implants, doi: 10.1097/MAO.0b013e3181e7117e, 2010.
Zhang, J. (2010). Design of Steerable Electrode Arrays and Optimal Insertion Path Planning for Robot-Assisted Cochlear Implant Surgeries. Phd Thesis, Department of Mechanical Engineering, Columbia University, New York City, NY.
Jones, B. A., and Walker, I. D. Kinematics for Multisection Continuum Robots. IEEE Transactions on Robotics 22, 1 (Dec. 2006), 43-57.
K. Xu and N. Simaan, "Intrinsic Wrench Estimation and Its Performance Index for Multisegment Continuum Robots," IEEE Transactions on Robotics, vol. 26, No. 3, pp. 555-561, Jun. 2010.
Xu, K. (2009). Design, Modeling and Analysis of Continuum Robots as Surgical Assistants with Intrinsic Sensory Capabilities. Phd Thesis, Columbia University).
Xu, K., Qiu, D. & Simaan, N (2011). A Pilot Investigation of Continuum Robots as a Design Alternative for Upper Extremity Exoskeletons. In IEEE International Conference on Robotics and Biomimmetics (ROBIO'2011), pp. 656-662.

(56) References Cited

OTHER PUBLICATIONS

Kesner, S. B., and Howe, R. D. Design and Control of Motion Compensation Cardiac Catheters. In 2010 IEEE International Conference on Robotics and Automation (Anchorage, AK, 2010), pp. 1059-1065.
Kesner, S. B., and Howe, R. D. Force Control of Flexible Catheter Robots for Beating Heart Surgery. In 2011 IEEE International Conference on Robotics and Automation (Shanghai, China, Jan. 2011), pp. 1589-1594.
Kesner, S. B., Howe, R. D., and Member, S. Position Control of Motion Compensation Cardiac Catheters. IEEE Transaction on Robotics 27, 6 (2011), 1045-1055.
Khatib, O. A Unified Approach for Motion and Force Control of Robot Manipulators: The Operational Space Formulation. IEEE Journal of Robotics and Automation 3, 1 (1987), 43-53.
Kragic, D., Marayong, P., Li-Ming Su, Okamura, A. M., and Hager, G. D. Human-Machine Collaborative Systems for Microsurgical Applications. The International Journal of Robotics Research 24,9 (Sep. 2005), 731-741.
Kwartowitz DM, Miga MI, Herrell SD, Galloway RL. Towards Image Guided Robotic Surgery: Multi-Arm Tracking Through Hybrid Localization. Int J Comput Assist Radiol Surg. May 2009;4(3):281-6. Epub Mar. 19, 2009.
L. B. Rosenberg, "Virtual fixtures: Perceptual tools for telerobotic manipulation," in Proceedings of IEEE Virtual Reality Annual International Symposium, 1993, pp. 76-82.
Lawson, G., Matar, N., Remacle, M., Jamart, J., and Bachy, V. Transoral robotic surgery for the management of head and neck tumors: learning curve. European archives of oto-rhino-laryngology : official journal of the European Federation of Oto-Rhino-Laryngological Societies (EUFOS) : affiliated with the German Society for Oto-Rhino-Laryngology—Head and Neck Surgery 268, 12 (Dec. 2011), 1795-801.
Lipkin, H., and Duffy, J. Hybrid Twist and Wrench Control for a Robotic Manipulator. Transaction of the ASME 110 (1988), 138-144.
Lock, J., and Dupont, P. E. Friction Modeling in Concentric Tube Robots. In 2011 IEEE International Conference on Robotics and Automation (Shanghai, China, Jan. 2011), pp. 1139-1146.
Lumelsky, V. J., and Cheung, E. Real-Time Collision Avoidance in Tele-operated Whole-Sensitive Robot Arm Manipulators. IEEE Transactions on Systems, Man, and Cybernetics 23, 1 (1993), 194-203.
M. Li and R. H. Taylor, "Spatial Motion Constraints in Medical Robot Using Virtual Fixtures Generated by Anatomy," 2004, pp. 1270-1275.
Ma, S., and Konno, M. An obstacle avoidance scheme for hyper-redundant manipulators—global motion planning in posture space. In Proceedings of Inter-national Conference on Robotics and Automation (1997), vol. 1, IEEE, pp. 161-166.
Mahvash, M., and Okamura, A. M. Friction Compensation for a Force-Feedback Telerobotic System. In 2006 IEEE International Conference on Robotics and Automation (Orlando, FL, 2006), No. May, pp. 3268-3273.
Mahvash, M., and Dupont, P. E. Mechanics of dynamic needle insertion into a biological material. IEEE transactions on bio-medical engineering 57, 4 (Apr. 2010), 934-43.
Mahvash, M., and Dupont, P. E. Stiffness Control of Surgical Continuum Manipulators. IEEE Transaction on Robotics 27, 2 (2011), 334-345.
Mason, M. T. Compliance and Force Control for Computer Controlled Manipulators. IEEE Transaction on Systems, Man, and Cybernetics smc-11, 6 (1981), 418-432.
Mason, M. T., and Salisbury, J. K. Robot Hands and the Mechanics of Manipulation. MIT Press, Cambridge, MA, 1985.
Matsumoto, T., and Kosuge, K. Collision Detection of Manipulator Based on Adaptive Control Law. In 2001 IEEE/ASME International Conference on Advanced Intelligent Mechatronics (Como, Italy, 2001), pp. 177-182.

N. Simaan, R. Taylor, and P. Flint, "A Dexterous System for Laryngeal Surgery—Multi-Backbone Bending Snake-like Slaves for Teleoperated Dexterous Surgical Tool Manipulation." pp. 351-357, 2004.
N. Simaan, R. Taylor, P. Flint, and A. Hillel, "Minimally Invasive Surgery of the Upper Airways: Addressing the Challenges of Dexterity Enhancement in Confined Spaces," Nova Scien, R. Faust, Ed. 2007, pp. 261-280.
N. Simaan, W. Wei, R. Goldman, H. Fine, and S. Chang, "A Dual-Arm Workstation for Intraocular Dexterity-Enhanced Microsurgery of the Eye and In-Organ Dexterity Enhancement and Manipulation of Suspended Organs," 2006.
N. Simaan and M. Shoham, "Geometric Interpretation of the Derivatives of Parallel Robot's Jacobian Matrix with Application to Stiffness Control" ASME Journal of Mechanical Design, vol. 125, pp. 33-42., doi: 10.1115/1.1539514, 2003.
N. Simaan and M. Shoham, "Singularity Analysis of a Class of Composite Serial In-Parallel Robots," IEEE transactions on Robotics and Automation, vol. 17, No. 3, pp. 301-311, doi:10.1109/70.938387 Jun. 2001.
N. Simaan and M. Shoham, "Stiffness Synthesis of a Variable Geometry Six Degrees-of-Freedom Double Planar Parallel Robot," International Journal of Robotics Research (IJRR), vol. 22, No. 9, pp. 757-775, doi: 10.1177/02783649030229005, Sep. 2003.
N. Simaan, K. Xu, W. Wei, A. Kapoor, P. Kazanzides, R. Taylor, P. Flint, "Design and Integration of a Telerobotic System for Minimally Invasive Surgery of the Throat," International Journal of Robotics Research (IJRR) special issue on medical robotics. doi: 10.1177/0278364908104278, vol. 28, No. 9, 1134-1153 , 2009.
Simaan, N., Manolidis, S. & Roland, J. T (2009). Inroads towards a robotically inserted CI electrode development. In 9th European Symposium of Paediatric Cochlear Implantation.
Simaan, N., Zhang, J., Roland, J. T. & Manolidis, S (2010). Steerable Continuum Robot Design for Cochlear Implant Surgery. In IEEE International Conference on Robotics and Automation Workshop on Snakes, Worms and Catheters: Continuum and Serpentine Robots for Minimally Invasive Surgery, May 3.
Simaan, N., Zhang, J., Roland, J. T. & Manolidis, S (2010). Robotic Study Shows that Insertion Speed Affects Cochlear Implant Electrode Insertion Forces. In the 11th International Conference on Cochlear Implants and other Implantable Auditory Technologies, Stockholm, Sweden, Jun. 30-Jul. 3.
Simaan, N., Zhang, J., Roland, J. T. & Manolidis, S (2011). Robotic System for Steerable Cochlear Implant Insertion. In 2011 National Congress of the Italian Society of Audiology & Phoniatrics in Bari, Italy.
Simaan, N (2012). Design Considerations and Lessons Learned in Developing Systems for Single Port Access Surgery and Natural Orifice Surgery. In 34th international Conference on Engineering in Medicine and Biology Society (mini-symposium on Robotic Single-Port Surgery and Notes). San Diego, Aug. 27-31, 2012.
Simaan, N., Bajo, A., Reiter, A., Long, W., Allen, P. & Fowler, D. (2013). Lessons learned using the insertable robotic effector platform (IREP) for single port access surgery. Journal of Robotic Surgery.
Nakamura, Y. Advanced Robotics: Redundancy and Optimization. Addison-Wesley Longman Publishing Co., Inc., Boston, MA, USA, 1990.
Park, J., and Khatib, O. Robot Multiple Contact Control. Robotica 26, 05 (2008), 667-677.
Penning, R. S., Jung, J., Borgstadt, J. A., Ferrier, N. J., and Michael, R. Towards Closed Loop Control of a Continuum Robotic Manipulator for Medical Applications. In 2011 IEEE International Conference on Robotics and Automation (Shanghai, China, 2011), pp. 4822-4827.
Petrovskaya, A., Park, J., and Khatib, O. Probabilistic Estimation of Whole Body Contacts for Multi-Contact Robot Control. In 2007 IEEE International Conference on Robotics and Automation (Rome, 2007), No. c, pp. 568-573.
Phee, S. J., Low, S. C., Sun, Z. L., Ho, K. Y., Huang, W. M., and Thant, Z. M. Robotic system for no-scar gastrointestinal surgery. The international journal of medical robotics+computer assisted surgery : MRCAS 4, 1 (Mar. 2008), 15-22.

(56) References Cited

OTHER PUBLICATIONS

Piccigallo, M., Scarfogliero, U., Quaglia, C., Petroni, G., Val-dastri, P., Menciassi, A., and Dario, P. Design of a Novel Bimanual Robotic System for Single-Port Laparoscopy. IEEE/ASME Transaction on Mechatronics 15, 6 (2010), 871-878.

Pile, J., Tsay, I. A., Dalton, J., Balachandran, R., Labadie, R. F. & Simaan, N (2012). Speed Dependence of Insertion Forces During CI Electrode Insertion. In Presented at the 12th Annual Conference on Cochlear Implants and other Implantable Auditory Technologies CI'2012, Baltimore, MD, May 3-5, 2012.

Pile, J. & Simaan, N (2013). Characterization of Friction and Speed Effects and Methods for Detection of Cochlear Implant Electrode Tip Fold-over. In Accepted for publication in IEEE International Conference on Robotics and Automation (ICRA'2013).

R.H. Sturges Jr and S. Laowattana, "A flexible, tendon-controlled device for endoscopy," 1991, vol. 3, pp. 2582-2591.

Raibert, M. H., and Craig, J. J. Hybrid Position/Force Control of Manipulators. Journal of Dynamic Systems, Measurement, and Control 103, 2 (1981), 126.

Reichert, S., Zhang, J., Xu, K, Simaan, N. & Manolidis, S (2007). Robotic insertion of cochlear implant electrodes to minimize cochlear trauma. In 6th European Congress of Oto-Rhino-Laryngology, Head and Neck Surgery., Vienna, Austria, Jun. 2007.

Robinson, G., and Davies, J. Continuum robots—a state of the art. In 1999 IEEE International Conference on Robotics and Automation (Detroit, MI, USA, 1999), vol. 4, Ieee, pp. 2849-2854.

Roland, J. T., Zhang, J., Manolidis, S. & Simaan, N (2009). Progress Towards a Robotically Inserted Cochlear Implant Electrode. In 12th Symposium on Cochlear Implants in Children, Seattle.

Rosenberg, L. Virtual fixtures: Perceptual tools for telerobotic manipulation. In Proceedings of IEEE Virtual Reality Annual International Symposium (1993) pp. 76-82.

Rucker, D. C., and Webster, III, R. J. Deflection-Based Force Sensing for Continuum Robots : A Probabilistic Approach. In 2011 IEEE/RSJ Inter-national Conference on Intelligent Robots and Systems (2011), pp. 3764-3769.

Rucker, D. C., Jones, B. A., and Webster III, R. J. A Geometrically Exact Model for Externally Loaded Concentric-Tube Continuum Robots. IEEE Transaction on Robotics 26, 5 (2010), 769-780.

S. J. Harris, W. J. Lin, R. D. Hibberd, J. Cobb, R. Middelton, and B. L. Davies, "Experiences with Robotic Systems for Knee Surgery," vol. 1205, J. Troccaz, E. Grimson, and R. Mosges, Eds. Springer, 1997, pp. 757-766.

Saito, S. Transurethral en bloc resection of bladder tumors. The Journal of urology 166, 6 (Dec. 2001), 2148-50.

Salemo, A., Zhang, J., Bhatla, A., Lyulko, O. V., Nie, J., Dutta, A. et al (2007). Design Considerations for a Minimally Invasive High-Throughput Automation System for Radiation Biodosimetry. In IEEE Conference on Automation Science and Engineering, pp. 846-852. Scottsdale, AZ, USA.

Salisbury, J. Active stiffness control of a manipulator in cartesian coordinates. In 1980 19th IEEE Conference on Decision and Control including the Symposium on Adaptive Processes (1980), pp. 95-100.

Seibold, U., Kubler, B., and Hirzinger, G. Prototype of Instrument for Minimally Invasive Surgery with 6-Axis Force Sensing Capability. In Proceedings of the 2005 IEEE International Conference on Robotics and Automation (Barcelona, Spain, 2005), 496-501, Ed., IEEE, pp. 496-501.

Sentis, L., Park, J., and Khatib, O. Compliant Control of Multicontact and Center-of-Mass Behaviors in Humanoid Robots. IEEE Transactions on Robotics 26, 3 (Jun. 2010), 483-501.

Shen, J.-H., Yu, H., Simaan, N. & Joos, K. M. (2013). A Robotic-controlled Intraocular OCT Probe. In 2013 The Association for Research in Vision and Ophthalmology Annual Conference (ARVO'2013).

Siciliano, B., Sciavicco, L., Villani, L., and Oriolo, G. Robotics: Modelling, Planning, and Control. 2009.

Su, H., Cardona, D. C., Shang, W., Camilo, A., Cole, G. A., Rucker, D. C., Webster, R. J., and Fischer, G. S. A MRI-Guided Concentric Tube Continuum Robot with Piezoelectric Actuation: A Feasibility Study. In 2012 IEEE International Conference on Robotics and Automation (St. Paul, MN USA, 2012), No. May.

Taylor, R., Jensen, P., Whitcomb, L., Barnes, A., Kumar, R., Stoianovici, D., Gupta, P., Wang, Z., DeJuan, E., and Kavoussi, L. A Steady-hand robotic system for microsurgical augmentation. International Journal of Robotics Research 18, 12 (1999), 1201-1210.

Torres, L. G., and Alterovitz, R. Motion Planning for Concentric Tube Robots Using Mechanics-based Models. In 2011 IEEE/RSJ International Con-ference on Intelligent Robots and Systems (San Francisco, CA, USA, 2011), pp. 5153-5159.

Ukai, R., Kawashita, E., and Ikeda, H. A new technique for transurethral resection of superficial bladder tumor in 1 piece. The Journal of Urology2 163, 3 (2000), 878-879.

Valdastri, P., Harada, K., Menciassi, A., Beccai, L., Stefanini, C., Fujie, M., and Dario, P. Integration of a miniaturised triaxial force sensor in a minimally invasive surgical tool. IEEE transactions on biomedical engineering 53, 11 (Nov. 2006), 2397-400.

W. Wei, R. Goldman, H. Fine, S. Chang, and N. Simaan, "Design and Dexterity Evaluation for a Dual-Arm Micro-Surgical Robotic System for Orbital Manipulation and Intraocular Dexterity," IEEE Transactions on Robotics, vol. 25, No. 1, pp. 147-157, 2009.

Wagner, C. R., Stylopoulos, N., Jackson, P. G., and Howe, R. D. The Benefits of Force Feedback in Surgery: Examination of Blunt Dissection. Presence: Teleoperators and Virtual Environments 16, 3 (2007), 252-262.

Webster III, R. J., Romano, J. M., and Cowan, N. J. Mechanics of Precurved-Tube Continuum Robots. IEEE Transaction on Robotics 25, 1 (2009), 67-78.

Webster III, R. J., and Jones, B. A. Design and Kinematic Modeling of Constant Curvature Continuum Robots: A Review. The International Journal of Robotics Research (Jun. 2010).

Wei Tech, A., Khosla, P., and Riviere, C. An Intelligent Hand-Held Microsurgical Instrument for Improved Accuracy. In 23rd Annual International Conference of the IEEE Engineering in Medicine and Biology Society (Istanbul, Turkey, 2001), pp. 25-28.

Wei, W., Goldman, R., Fine, H., Chang, S., Simaan, N., "Performance Evaluation for Multi-Arm Manipulation of Hollow Suspended Organs," IEEE Transactions on Robotics, vol. 25, No. 1, pp. 147-157, doi 10.1109/TRO.2008.2006865, 2009.

Wei, W., Simaan N., "Design of Planar Parallel Robots With Preloaded Flexures for Guaranteed Backlash Prevention," ASME Journal of Mechanisms and Robotics (JMR), doi:10.1115/1. 4000522, vol. 2, No. 1, pp. 011012-1 to 011012-10, 2010.

Wei, W. (2010). Design and Implementation of High-Precision Hybrid Robotic Systems with Application for Ophthalmic Micro-Surgery. Phd Thesis, Department of Mechanical Engineering, Columbia University, New York City, NY.

Wei, W., Fine, H., Chang, S. & Simaan, N (2010). A Pilot Study on Using a Flexible Cannula Robot for Micro-Vascular Stenting. In IEEE International Conference on Robotics and Automation Workshop on Snakes, Worms and Catheters: Continuum and Serpentine Robots for Minimally Invasive Surgery, IEEE International Conference on Robotics and Automation, May 3.

Weinstein, G. S., O'Malley, B. W., Magnuson, J. S., Carroll, W. R., Olsen, K. D., Daio, L., Moore, E. J., and Holsinger, F. C. Transoral robotic surgery: A multicenter study to assess feasibility, safety, and surgical margins. The Laryngoscope (Jul. 2012), 1-7.

Whitney, D. E. Force Feedback Control of Manipulator Fine Motions. Journal of Dynamic Systems, Measurement, and Control 99, 2 (1977), 91.

Whitney, D. E. Resolved Motion Rate Control of Manipulators and Human Prostheses. IEEE Transaction on Man-Machine Systems MMS-10, 2 (Jun. 1969), 47-53.

Yoshikawa, T. Force Control of Robot Manipulators. In 2000 IEEE International Conference on Robotics and Automation (San Francisco, CA, USA, 2000), No. April, pp. 220-226.

Yu, H., Shen, J. H., Joos, K. M. & Simaan, N (2013). Design , Calibration and Preliminary Testing of a Robotic Telemanipulator for OCT guided Retinal Surgery. In Accepted for publication in IEEE International Conference on Robotics and Automation (ICRA'2013).

(56) References Cited

OTHER PUBLICATIONS

Zhou, J., Shen, X., Petriu, E. M., and Georganas, N. D. Linear Velocity and Acceleration Estimation of 3 DOF Haptic Interface. In IEEE International Workshop on Haptic Audio Visual Environments and their Application (HAVE 2008) (Ottawa, Canada, 2008), pp. 137-142.

Bajo, A., Goldman, R. E., Wang, L., Fowler, D. & Simaan, N (2012). Integration and Preliminary Evaluation of an Insertable Robotic Effectors Platform for Single Port Access Surgery. In International Conference on Robotics and Automation (ICRA'2012), pp. 3381-3387.

Bajo, A., Pickens, R. B., Herrell, D. S. & Simaan, N (2012). A Pilot Ex-Vivo Evaluation of a Telerobotic System for Transurethral Intervention and Surveillance. In Hamlyn Symposium on Medical Robotics.

Bajo, A., Pickens, R. B., Harrell, D. S. & Simaan, N (2013). Constrained Motion Control of Multisegment Continuum Robots for Transurethral Bladder Resection and Surveillance. In Accepted for publication in IEEE International Conference on Robotics and Automation (ICRA'2013).

A. Kapoor, K. Xu, W. Wei, N. Simaan, and R. Taylor, "Telemanipulation of Snake-Like Robots for Minimally Invasive Surgery of the Upper Airway," in MICCAI 2006 workshop on medical robotics, 2006.

A. Kapoor, N. Simaan, and P. Kazanzides, "A System for Speed and Torque Control of DC Motors with Application to Small Snake Robots," 2004.

A. Kapoor, N. Simaan, and R. Taylor, "Suturing in Confined Spaces: Constrained Motion Control of a Hybrid 8-DoF Robot", in IEEE Conference on Advanced Robotics, 2005, pp. 452-459.

Abbott, J., Marayong, P., and Okamura, A. M. Haptic virtual fixtures for robot-assisted manipulation. Robotics Research 28, Aug. 2007, 49-64.

Alexander T. Hillel, Ankur Kapoor, Nabil Simaan, Russell H. Taylor and Paul Flint, "Applications of Robotics for Laryngeal Surgery," Otolaryngologic Clinics of North America, Nasir Bhatti & Ralph P. Tufano Eds., vol. 41, Issue 4, pp. 781-791, doi:0.1016/j.otc.2008.01.021, Aug. 2008.

Chen, Y., Zhang, J., Wang, H., Garty, G., Xu, Y., Lyulko, O., Turner, H., Randers-Pehrson, G., Simaan, N., Yao, L., Brenner, D., "Development of a Robotically-based Automated Biodosimetry Tool for Highthroughput Radiological Triage," accepted in International Journal of Biomechatronics and Biomedical Robotics (IJBBR), vol. 1, No. 2 pp. 115-125, 2010.

Debus, T., Dupont, P., and Howe, R. Contact State Estimation using Multiple Model Estimation and Hidden Markov Models. 2The International Journal of Robotics Research 23, 4-5 (2004), 399-413.

Ding, J., Xu, K., Goldman, R. E., Allen, P. K., Fowler, D. L., and Simaan, N. "Design, Simulation and Evaluation of Kinematic Alternatives for Insertable Robotic Effectors Platforms in Single Port Access Surgery," In 2010 IEEE International Conference on Robotics and Automation (Anchorage, AK, 2010), pp. 1053-1058.

Godage, Isuru S. et al., "Shape Function-Based Kinematics and Dynamics for Variable Length Continuum Robotic Arms," 2011 IEEE International Conference on Robotics and Automation (May 9-13, 2011).

R. E. Goldman, A. Bajo, and N. Simaan, "Compliant Motion Control for Continuum Robots with Intrinsic Actuation Sensing," in IEEE International Conference on Robotics and Automation, 2011, pp. 1126-1132.

Gravagne, Ian A. and Ian D. Walker, "Manipulability, Force, and Compliance Analysis for Planar Continuum Manipulators," IEEE Transactions on Robotics and Automation, vol. 18, No. 3 (Jun. 2002).

Gravagne, Ian A. et al, "Good Vibrations: A Vibration Damping Setpoint Controller for Continuum Robots," Proceedings of the 2001 IEEE International Conference on Robotics & Automation (May 21-26, 2001).

Hamid, S. A. & Simaan, N (2009). Design and Synthesis of Wire-Actuated Universal-Joint Wrists for Surgical Applications. In 2009 IEEE International Conference on Robotics and Automation, pp. 1807-1831. Kobe, Japan.

Hannan, M. W., and Walker, I. D. Kinematics and the Implementation of an Elephant's Trunk Manipulator and Other Continuum Style Robots. Journal of Robotic Systems 20, 2 (2003), 45-63.

Hayward, Vincent, "Fast Collision Detection Scheme by Recursive Decomposition of a Manipulator Workspace," Proceedings IEEE International Conference on Robotics and Automation, vol. 3 (1986).

Hogan, N. Impedance Control: An Approach to Manipulation: Part ITheory. Journal of Dynamic Systems, Measurement, and Control 107, 1 (1985), 1.

International Search Report and Written Opinion for PCT Application No. PCT/US2013/021167 dated Mar. 22, 2013.

International Search Report and Written Opinion for PCT Application No. PCT/US2013/037336 dated Jul. 25, 2013.

International Search Report and Written Opinion for PCT Application No. PCT/US2013/037346 dated Aug. 27, 2013.

International Search Report and Written Opinion for PCT Application No. PCT/US2013/037353 dated Aug. 19, 2013.

International Search Report and Written Opinion for PCT Application No. PCT/US2013/039280 dated Aug. 20, 2013.

J. Ding, K. Xu, R. Goldman, P. Allen, D. Fowler, and N. Simaan, "Design, Simulation and Evaluation of Kinematic Alternatives for Insertable Robotic Effectors Platforms in Single Port Access Surgery." pp. 1053-1058, 2010.

J. J. Abbott and A. M. Okamura, "Stable Forbidden-Region Virtual Fixtures for Bilateral Telemanipulation," vol. 128, No. 1, pp. 53-64, 2006.

J. Zhang. S. Bhattacharyya, and N. Simaan, "Model and Parameter Identification of Friction During Robotic Insertion of Cochlear-Implant Electrode Arrays," in IEEE International Conference on Robotics and Automation, 2009, pp. 3859-3864.

Jones, Bryan A., "Kinematics for Multisection Continuum Robots," IEEE Transactions on Robotics, vol. 22, No. 1 (Feb. 2006).

K. Xu and N. Simaan, "Actuation Compensation for Flexible Surgical Snake-like Robots with Redundant Remote Actuation," in IEEE International Conference on Robotics and Automation, 2006, pp. 4148-4154.

K. Xu and N. Simaan, "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.

K. Xu, R. Goldman, J. Ding, P. Allen, D. Fowler, and N. Simaan, "System Design of an Insertable Robotic Effector Platform for Single Port Access (SPA) Surgery," in IEEE/RSJ International Conference on Intelligent Robots and Systems, 2009, pp. 5546-5552.

K. Xu and N. Simaan, "An Investigation of the Intrinsic Force Sensing Capabilities of Continuum Robots," IEEE Transactions on Robotics (TRO), vol. 23, No. 3 (Jun. 2008).

Mahvash, Mohsen and Pierre E. Dupont, "Stiffness Control of a Continuum Manipulator in Contact with a Soft Environment," The 2010 IEEE/RSJ International Conference on Intelligent Robots and Systems (Oct. 18-22, 2010).

Mahvash, Mohsen and Pierre E. Dupont, "Stiffness Control of Surgical Continuum Manipulators," IEEE Transactions on Robotics, vol. 27, No. 2 (Apr. 2011).

N. Simaan, A. Bajo, A. Reiter, L. Wang, P. Allen, and D. Fowler, "Lessons learned using the insertable robotic effector platform (IREP) for single port access surgery," Journal of Robotic Surgery, Apr. 2013.

N. Simaan, "Snake-Like Units Using Flexible Backbones and Actuation Redundancy for Enhanced Miniaturization," In 2005 IEEE International Conference on Robotics and Automation (Barcelona, Spain, 2005), IEEE, pp. 3023-3028.

N. Simaan, Russell H. Taylor, Paul Flint, "High Dexterity Snake-like Robotic Slaves for Minimally Invasive Telesurgery of the Upper Airway," MICCAI 2004 (7th International Conference on Medical Image Computing and Computer-Assisted Intervention), pp. 17-24, vol. 2, Saint Malo, France, Sep. 26-30, 2004.

(56) References Cited

OTHER PUBLICATIONS

Simaan, N., Glozman, D. & Shoham, M (1998). Design Considerations of New Six Degrees-of-Freedom Parallel Robots. In IEEE International Conference on Robotics and Automation (ICRA'1998), pp. 1327-1333.

Simaan, N. (1999). Analysis and Synthesis of Parallel Robots for Medical Applications. Master Thesis, Technion-Israel Institute of Technology, Haifa, Israel.

N. Simaan, Task-Based Design and Synthesis of Variable Geometry Parallel Robots (2002). Phd Thesis, Technion-Israel Institute of Technology, Haifa, Israel.

Pickens, R. B., Bajo, A., Simaan, N. & Herrell, S. D (2012). Preliminary Testing of a Transurethral Dexterous Robotic System for Bladder Resection. In 27th EUS Annual Meeting, pp. 65. Atlanta, GA.

Pile, J., Cheung, M.-Y., Zhang, J. & Simaan, N (2011). Algorithms and Design Considerations for Robot Assisted Insertion of Perimodiolar Electrode Arrays. In 2011 IEEE International Conference on Robotics and Automation. Shanghai, China.

R. Taylor et al., "Steady-hand robotic system for microsurgical augmentation," International Journal of Robotics Research, vol. 18, No. 12, pp. 1201-1210, 1999.

Reiter, A., Bajo, A., Iliopoulos, K., Simaan, N., and Allen, P. K. Learning-Based Configuration Estimation of a Multi-Segment Continuum Robot. In the Fourth IEEE RAS/EMBS International Conference on Biomedical Robotics and Biomechatronics (Roma, Italy, 2012), p. accepted.

Reiter, A., Goldman, R. E., Bajo, A., Iliopoulos, K., Simaan, N., and Allen, P. K. A Learning Algorithm for Visual Pose Estimation of Continuum Robots. In 2011 IEEE/RSJ International Conference on Intelligent Robots and Systems (San Francisco, CA, USA, 2011), pp. 2390-2396.

Rivera-Serrano, C. M., Johnson, P., Zubiate, B., Kuenzler, R., Choset, H., Zenati, M., Tully, S., and Duvvuri, U. A transoral highly flexible robot: Novel technology and application. The Laryngoscope 122, 5 (May 2012), 1067-71.

Sen, T. H., Deshmukh, N., Roger E, .. G., Kazanzides, P., Taylor, R. H., Boctor, E. et al (2012). Enabling technologies for natural orifice transluminal endoscopic surgery (N.O.T.E.S) using robotically guided elasticity imaging. In Proceeding of SPIE Medical Imaging 2012, pp. 83161Y1-83161Y8.

Tully, S., Bajo, A., Kantor, G., Choset, H., and Simaan, N. Constrained Filtering with Contact Detection Data for the Localization and Registration of Continuum Robots in Flexible Environments. In 2012 IEEE International Conference on Robotics and Automation (St. Paul, MI USA, 2012).

International Search Report, PCT/US2013/037353, dated Aug. 19, 2013.

Written Opinion, PCT/US2013/037353, dated Aug. 19, 2013.

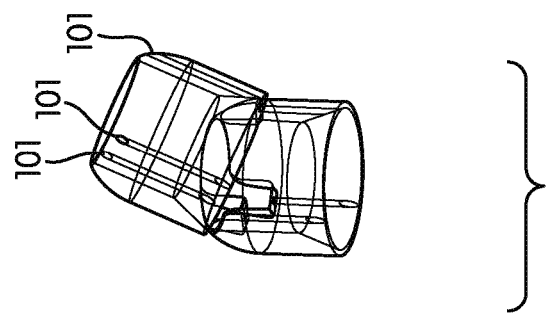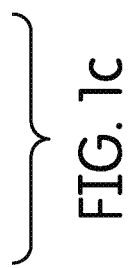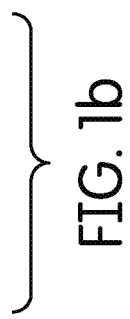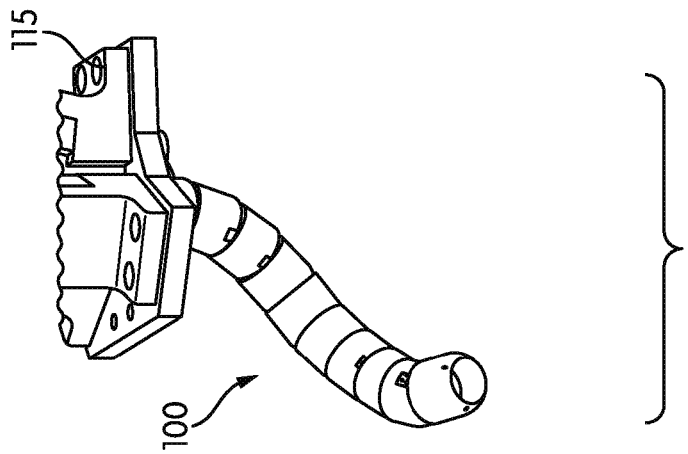

ROBOTIC DEVICE FOR ESTABLISHING ACCESS CHANNEL

RELATED APPLICATIONS

This application claims priority to U.S. Provisional Application No. 61/636,506, filed on Apr. 20, 2012 and titled "APPARATUS AND METHODS FOR QUICK AND SAFE DEEP ACCESS INTO MAMMALIAN ANATOMY," the entire contents of which are incorporated herein by reference.

STATEMENT REGARDING FEDERALLY SPONSORED RESEARCH OR DEVELOPMENT

This invention was made with government support under grant IIS-1063750 awarded by the National Science Foundation. The government has certain rights in the invention.

FIELD OF THE INVENTION

The present invention relates to devices and methods for manipulating continuum segment robots. More specifically, the present invention relates to devices and methods for bracing continuum segment robots having an access channel therewith with respect to surrounding anatomy.

BACKGROUND OF THE INVENTION

Natural orifice transluminal endoscopic surgery (NOTES) is preferred over traditional open body surgery because the latter leaves scars, is prone to causing infection of access incision sites, and use of access incisions is associated with increased risk for hernia and formation of adhesions. In addition, natural orifice surgery is an improvement over minimally invasive surgery (MIS), which uses 3-5 access incisions with each incision associated with a scar, risk for infection, and risk for hernia. In natural orifice surgery, the operating site is reached via a natural opening. Also, in single port access surgery (SPAS) a single small incision is used to provide access to the anatomy.

SUMMARY OF THE INVENTION

An embodiment of the present invention provides a medical robot that includes a flexible, steerable, and selectively lockable channel. The medical robot is remotely actuated to enable the robot to move into an anatomical cavity and is then locked into place once the distal end of the robot reaches a desired location. The channel serves as a stable passageway through which users (i.e., surgeons) can deploy and guide other surgical tools or medical robots. The flexible, steerable channel increases the operating range for the surgeon and prevents damage to healthy tissue during a procedure. The walls of the device surrounding the channel have a minimal outer to inner diameter ratio to achieve a desired bore clearance.

Various constructions reduce mechanical complexity by providing a passively compliant and actively locking channel for deep access. Constructions are also able to increase the available channel bore for a device with a given external diameter by eliminating internal and external locking channels that would be required for devices with more extensive wire-actuation systems. Some embodiments of the invention use flexible NiTi backbones and acts as a continuum robot when it is in a passively compliant mode. As such, the robot maintains the orientation of its tip (i.e., the distal end of the channel) despite change in the shape of its body. In some embodiments, the orientation of the robot tip is steerable using a joystick and vision feedback. Additionally, because the robot acts as a continuum robot, it is compatible with other devices and methods developed for robot manipulation (e.g., devices and methods for force sensing and contact detection).

Some embodiments of the invention provide a support platform for deployment of flexible endoscopes and robots through the central channel. In some embodiments, the device can be used to provide safe access for deployable trocars, laryngoscopes (i.e., for laryngeal surgery), trans-oral (i.e., endoscopic gastric surgery), trans-esophageal procedures (i.e., for treating Barrett's disease), trans-nasal (i.e., surgery of the upper airways), and trans-anal/trans-vaginal stabilization platforms.

Additionally, some embodiments or this device are used in conjunction with an automatic steering system to appropriately guide the tip. In some embodiments, the steering system includes a forward looking vision module having optic flow vision methods. In some embodiments, the steering system also includes contact and load sensors mounted in a circumferential array about the tip. Additional joint level force information is used by the steering system to initiate compliant motion control.

In one embodiment, the invention provides a device for establishing an access channel to a target location. The device includes a plurality of cylindrical segments. Each segment includes a first end, a second end, a central bore, and a plurality of backbone channels. The first end of each cylindrical segment is convex-shaped relative to the second end. A plurality of backbones each extends through one of the backbone channels of each segment to join the plurality of segments together. The first end of one cylindrical segment is at least partially received by the second end of a second cylindrical segment. When joined together, the central bore of each of the plurality of cylindrical segments align to form an access channel. A distal segment is fixedly attached to each of the plurality of backbones such that an orientation of the distal segment can be adjusted by linear movement of one or more of the plurality of backbones through the plurality of cylindrical segments. Furthermore, when linear movement of the plurality of backbones is restricted, the shape of the access channel can be adjusted by external forces while maintaining the orientation of the distal segment.

In some embodiments, the device further includes a brace mechanism that extends radially from the access channel and contacts an interior wall of a structure to anchor the access channel relative to the structure. In some embodiments, the device further includes a locking mechanism to restrict angular movement of the cylindrical segments relative to each other. In some embodiments, the locking mechanism includes a rotatable shaft with a plurality of teeth on a first side and a smooth surface on a second side. The rotatable shaft is positioned through a shaft channel in each of the cylindrical segments. Each cylindrical segment includes a locking tab biased towards the center of the shaft channel such that the locking tab engages the rotatable shaft when the teeth are positioned proximate to the locking tab and disengages the rotatable shaft is rotated such that the smooth surface of the rotatable shaft is positioned proximate to the locking tab.

In another embodiment, the invention provides a method for establishing an access channel to a target location in an anatomical structure. A passively flexible device is inserted into an orifice of a patient and a distal end of the passively flexible device is positioned at a target location inside the anatomy. The passively flexible device is then braced to anatomical features at the target location to lock the passively flexible device and to define the shape of the access channel to the target location.

Other aspects of the invention will become apparent by consideration of the detailed description and accompanying drawings.

BRIEF DESCRIPTION OF THE DRAWINGS

FIGS. 1a-1d illustrate a device defining an access channel and including a backbone and a plurality of interconnected segments according to one embodiment of the present invention.

DETAILED DESCRIPTION

Figure 2A:
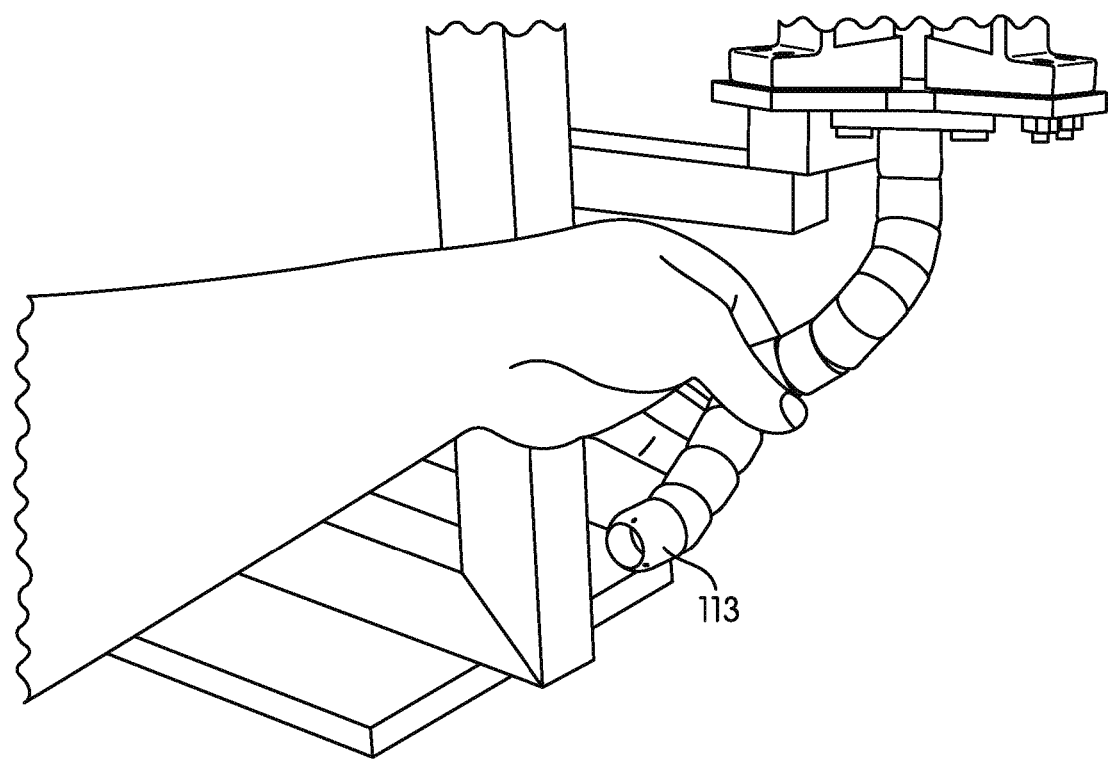
FIGS. 2a-2c illustrate the device of FIGS. 1a-1d including a tip that maintains a constant orientation.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

FIGS. 1a-1d illustrate a device 100 (i.e., a robot) that provides deep access into an anatomical cavity. The device 100 is both actively steerable and passively compliant. The robot 100 includes a plurality of backbones or wires 101 for positioning and manipulating the robot 100. The backbones/wires 101 pass through a plurality of interconnected or interlinked segments 103. In one construction, the backbones 101 are constructed of super-elastic NiTi (nickel titanium). Each of the segments 103 includes a wall defining a central bore or channel 105. The wall includes a thickness of material, an inner surface, and an outer surface. Each of the segments also includes a first end 107 and a second end 109. The first end 107 is convex-shaped relative to the second end 109. Consecutive segments 103 are coupled or linked together such that the second end 109 of one segment at least partially receives the first end 107 of an adjacent segment. The wall includes a recess 111 formed therein at the first end (i.e., near the convex-shaped end). In other constructions, the recess can be positioned in other locations on the wall including shapes other than that illustrated in FIGS. 1a-1d. The recess 111 allows for stress relief of the superelastic NiTi wires 101. The construction of the robot 100 illustrated in FIGS. 1a-1d is manipulated by three backbones (i.e., three recesses 111 and three channels that each correspond to one of three wires 101). In other constructions, the robot 100 could include additional backbones and, therefore, additional recesses and channels formed in the wall of each segment.

A distal segment forms the tip of the robot 113 while the proximal segment is rigidly attached to an external mount 115. The super-elastic backbones 101 pass through channels formed with the wall of each segment 103 and attach at the distal tip 113 of the distal segment. The rigidity of the tip 113, which is sustained by frictional moments between the consecutive segments, maintains the shape of the channel 105 when the device 100 is locked by pulling on the backbones 101. When the channel 105 is in a relaxed state the backbones 101 are incrementally released such that frictional forces between subsequent segments are small and the shape of the access channel 105 may be changed by external forces or constraints from the anatomy.

Figure 2B:
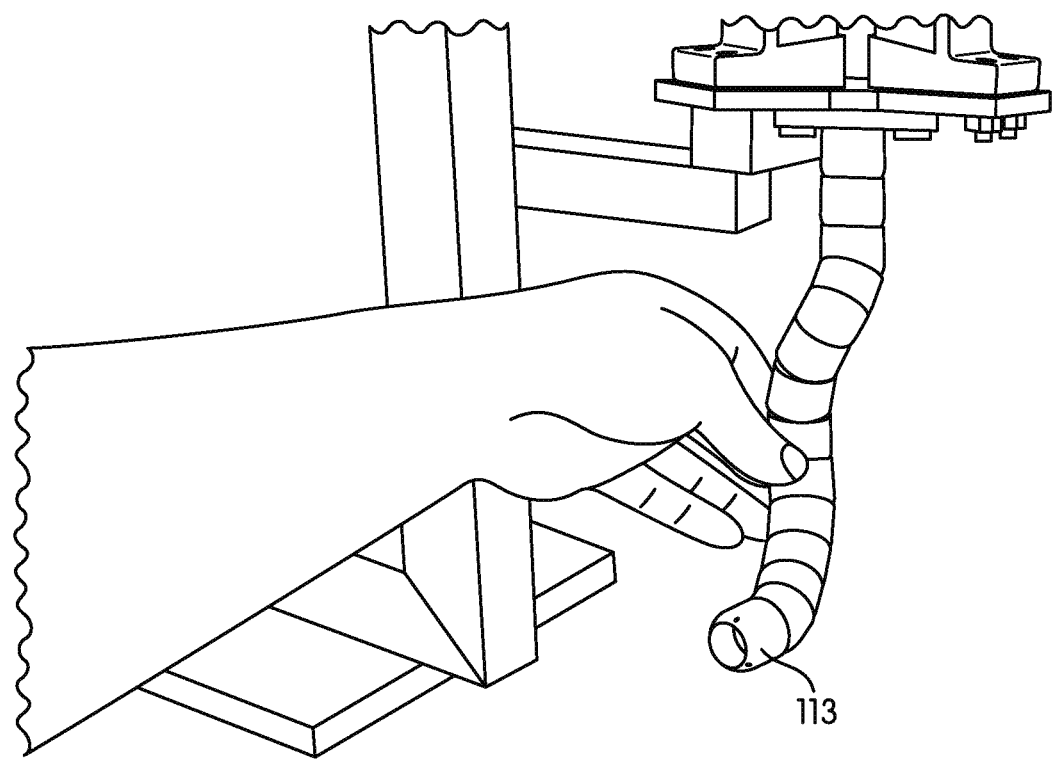
Figure 2C:
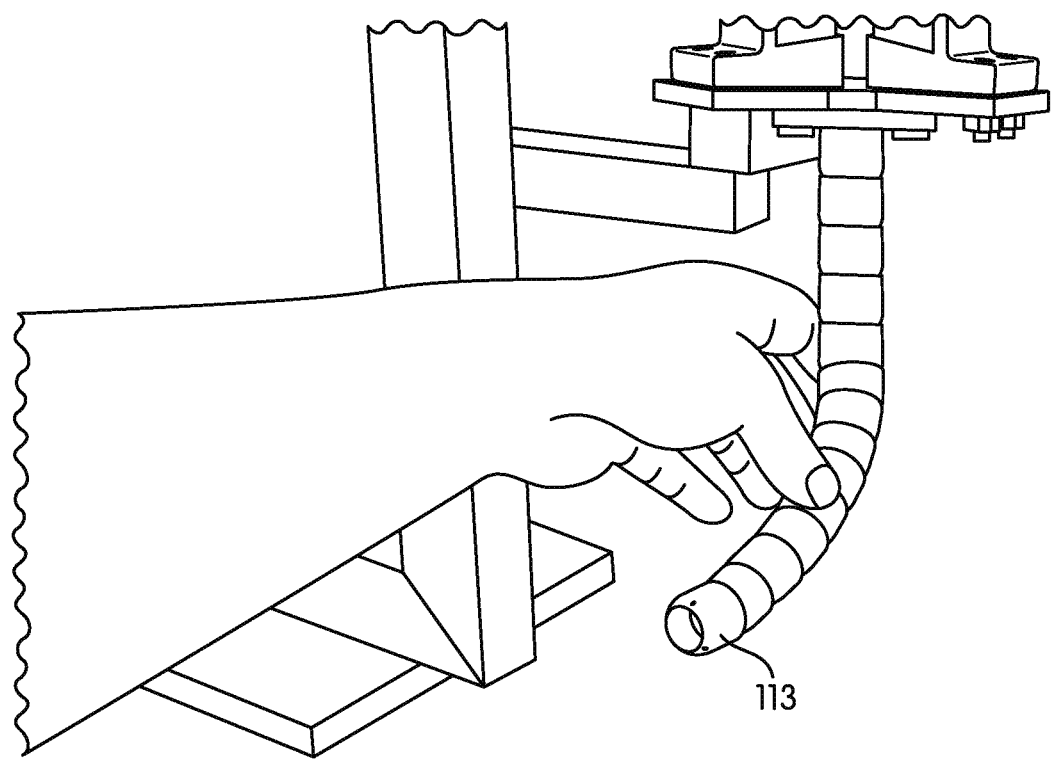

As illustrated in FIGS. 2a-2c, when in a relaxed state, changes in the shape of the access channel 105 cause a corresponding change in the position of the tip 113. However, the orientation of the tip 113 remains constant in space. This design acts as a generalized Shoenflies motion generator in a manner similar to the way parallelogram mechanisms are used to keep the orientation of a lamp fixed in space despite movement of the desk lamp.

Figure 3:
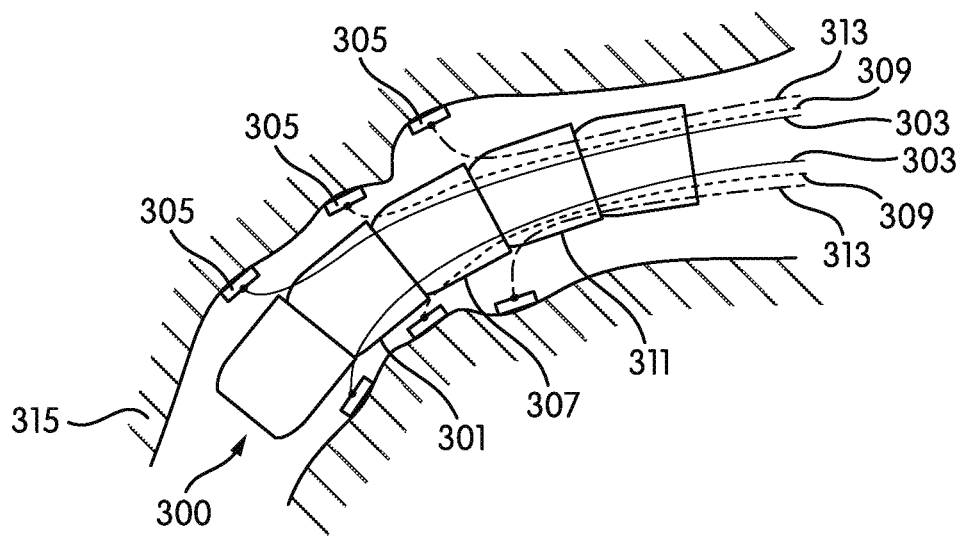
FIG. 3 illustrates the device of FIGS. 1a-1d including a first example of a brace mechanism.
Figure 4:
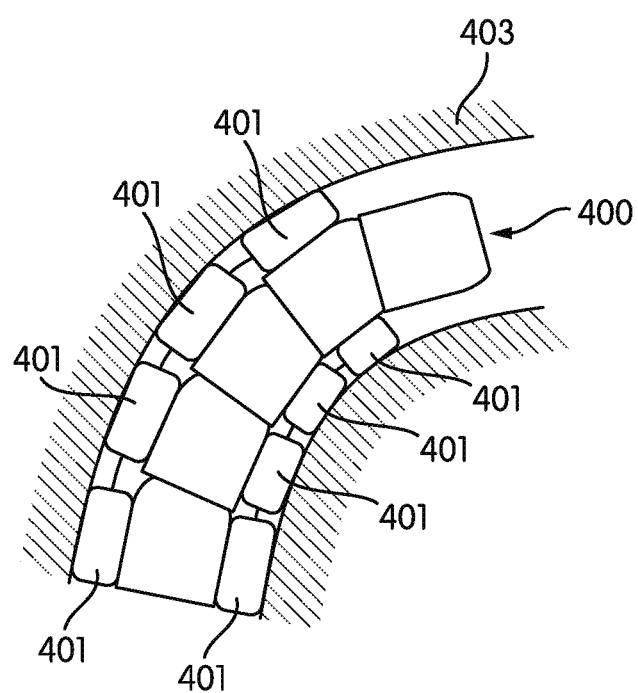
FIG. 4 illustrates the device of FIGS. 1a-1d including a second example of a brace mechanism.

Once the distal tip 113 of the device illustrated in FIGS. 1a-1d is positioned at a target location, the channel 105 provides a mechanism for safe and reliable access to the target location. Various tool including, for example, endoscopes can be inserted through the channel 105. To further stabilizes the device, in some constructions, the segments that form the channel 105 are locked into place and braced against the surrounding anatomy. FIGS. 3 and 4 illustrate two examples of mechanisms for providing circumferential bracing of the device. The robots illustrated in FIGS. 3 and 4 are modifications of the robot illustrated in FIGS. 1a-1d. Therefore, the illustrations and discussion below focus on the modifications.

Like the example of FIGS. 1a-1d, the robot 300 illustrated in FIG. 3 includes a plurality of backbones or wires that pass through interconnected or interlinked segments. The backbones/wires control the position and orientation of the distal tip of the robot. In this example, the backbones are comprised of one or more Kevlar strands or stainless steel wire rope with low bending resistance. Some or all of the segments include one or more additional channels or grooves formed within the wall. The additional channels can be formed entirely within the wall or can be formed as grooves along the inner surface of the wall exposed to the channel bore. In some embodiments, the additional channel is partially formed within the wall and partially exposed to the bore. Each additional channel/groove includes an aperture in communication with the recess for guiding superelastic NiTi wires or other components of a bracing mechanism through a segment of the device.

In the example of FIG. 3, the bracing mechanism includes a series of six NiTi wires running through the interior channel of the device 300. A first segment 301 includes a pair of channels oriented opposite one another on the inner surface of the segment 301. The first pair of NiTi wires 303 are positioned in the channels of the first segment 301. A support pad 305 is attached to the distal end of each NiTi wire 303. Similar pairs of channels are formed in a second segment 307 for receiving a second pair of NiTi wires 309 and in a third segment 311 for receiving a third pair of NiTi wires 313. Bracing of the device is achieved by pushing the pre-shaped NiTi wires through the channels of each segment such that they extend radially. This extension of the NiTi wires moves each support pad 305 into contact with the surrounding anatomy 315.

The pre-shaped NiTi wires in FIG. 3 may be pushed with an equal force for each wire by using external pistons connected to a hydraulic/pneumatic source with a common pressure used to actuate all pistons. Alternatively, the pre-shaped NiTi wires in FIG. 3 may be pushed with an equal force for each wire by externally pushing them through linear actuators connected to constant force springs connected in series with the NiTi wires supporting the bracing pads.

The robot 400 illustrated in FIG. 4 is similar to the robot in FIG. 3. However, the additional access channels used in FIG. 3 for moving the support pads 305 into contact with the surrounding anatomy are used in FIG. 4 to provide access to pneumatic pressure channels. The pneumatic pressure channels inflate circumferential balloons 401 for bracing the channel against anatomy.

In operation, the robot in FIG. 4 is guided within a conduit or pathway of the anatomy 403. The conduit or pathway of the anatomy may be tubular in shape or have irregular boundaries, irregular diameters along its length, or irregularly shaped and sized circumferences along its length. Once the robot is appropriately positioned, the pneumatic pressure source forces the balloons through the recesses in the first end of the segments such that the balloons are circumferentially inflated and anchor to the surrounding anatomy 403. The balloons 401 brace the device 400 against the surrounding anatomy 403 by expanding to fill excess space therebetween. The braced device provides a safe and reliable channel for positioning medical tools (e.g., snake-like robots and endoscopes) to a target location. The braced device also enhances the ability to manipulate devices by supporting the distal end of the devices thereby increasing precision during a procedure.

Figure 5:
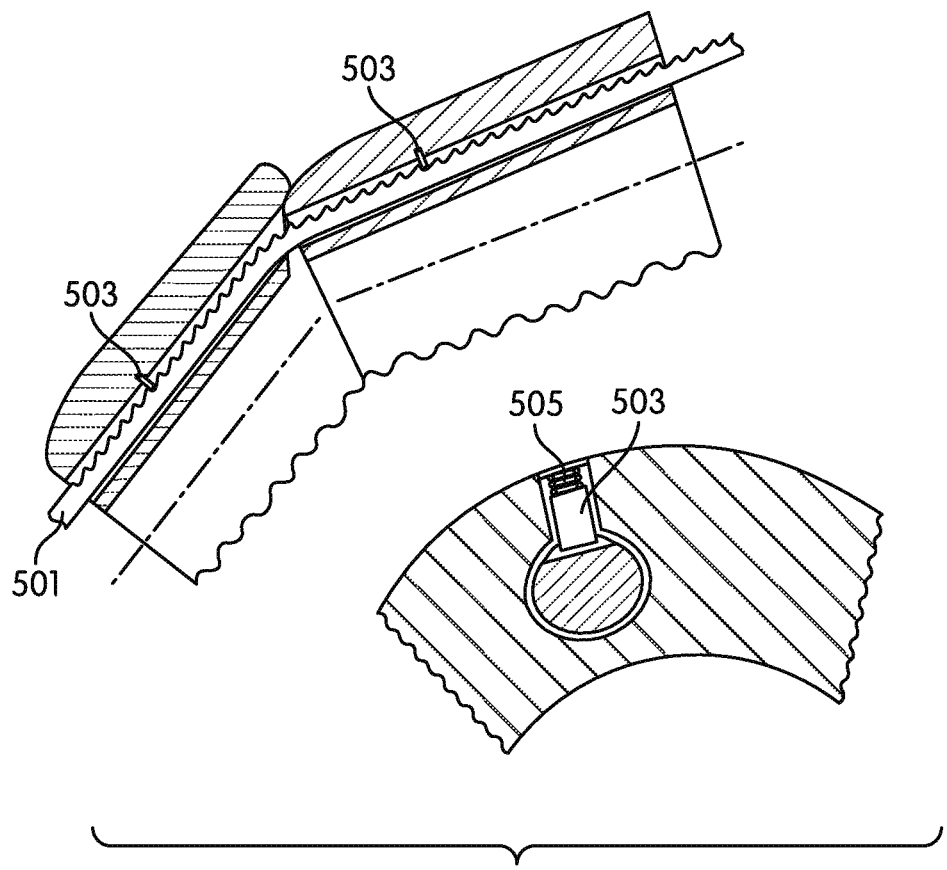
FIG. 5 illustrates the device of FIGS. 1a-1d including a locking mechanism.

FIG. 5 illustrates a locking mechanism of the device of FIGS. 1a-1d in further detail. The locking mechanism stiffens the otherwise flexible channel thereby increasing the channels rigidity once it has been appropriately positioned within the anatomy. The inner surface of the walls of each segment includes one or more additional channels for receiving a rotatable lock shaft 501 and at least one biased lock tab 503 for each channel. Although FIG. 5 illustrates only a single additional channel for in each segment for receiving one rotatable lock shaft 501, some constructions will include additional rotatable lock shafts positioned around the circumference of each segment to provide for increased rigidity of the device when locked.

Each lock shaft 501 is constructed of a flexible material such that its position and shape can change with the movement of the channel tube of the robotic device. As further illustrated in FIG. 6, the rotatable lock shaft 501 includes a plurality of teeth 601 formed on a single side of the rotatable lock shaft. The opposite side of the lock shaft 501 is smooth. The rotatable lock shaft is formed of a plurality of segments including a first lock shaft segment 603 and a segment lock shaft segment 605.

FIG. 5 illustrates the device with the locking mechanism engaged. Once the robot is appropriately positioned, the lock shaft 501 is rotated such that the teeth 601 engage the lock tab 503 in each segment. As further illustrated in the cross-sectional insert of FIG. 5, each lock tab 503 is biased by a spring 505 such that it engages the teeth 601 of the lock shaft 501. With the lock tabs 503 engaged with the teeth 601 of the lock shaft 501 lateral movement of the individual segments relative to the lock shaft 501 is prevented. As such, angular movement of each segment relative to the other segments is also prevented. To disengage the locking mechanism, the lock shaft 501 is rotated such that the smooth side of the lock shaft 501 contacts the lock tabs 503. The lock tabs 503 do not engage the smooth surface of the lock shaft 501 and, as such, angular movement of the individual segments is not restricted by the lock shaft 501.

Figure 6:
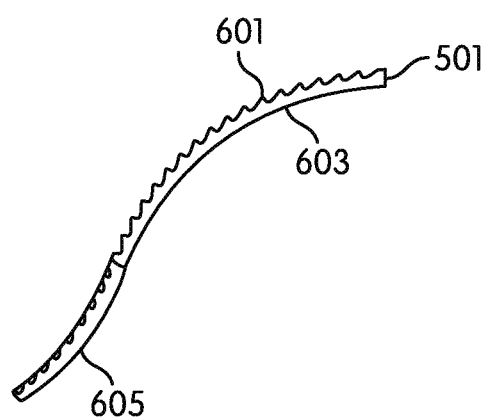
FIG. 6 illustrates an enlarged view of a portion of the locking mechanism of FIG. 5.

The lock shaft 501 illustrated in FIGS. 5 and 6 includes a first segment 603 and a second segment 605. In some constructions, the segments are independently rotatable such that portions of the device can be locked independently of the device as a whole. In other constructions, the lock shaft 501 may contain even more independent segments. Furthermore, although the example of FIG. 6 illustrates the teeth 601 all arranged on the same side of the lock shaft 501, in still other constructions, the teeth 601 can be arranged on different surfaces to implement more advanced locking configurations such as, for example, phase shifting.

Each of the constructions described above provides a device for establishing a safe, quick, and reliable access channel to a target location. As described above, the device includes a passively flexible robot with a controllable distal tip. In some constructions, the device is designed to operate with an auxiliary continuum robot system that is inserted through the access channel once the primary robot is properly placed and locked/braced within the anatomy. When used together, the primary robot described above enables quick deployment of the auxiliary robot to a target location and enables real-time feedback about patient outcome as it may be implemented with a highly localized anesthetic. When used together, the two robot systems are able to provide online feedback via optical coherence tomography and ultrasound probes. Further, constructions that include force-sensing capabilities are able to palpate tissue by actively moving the joint and measuring forces of constraint to discern various conditions such as arytenoids joint constraint. The result of discerning these conditions is that intra-surgical treatment plans can be designed and carried out. The two robotic systems are capable of being used in more precise deployment of chemotherapy to the lungs as well.

It should be noted that while each of the embodiments discussed herein are implemented automatically by robotic technology. However, each of the embodiments could be manually operated as well. Furthermore, although the technologies are described above in the context of minimally invasive or NOTES procedures within anatomical structures, other constructions may be used in non-surgical settings where a safe and reliable access channel to a target site within an orifice is desired.

Thus, the invention provides, among other things, a device and method for securing a flexible channel within the anatomy thereby providing a pathway that protects surrounding tissue by guiding additional tools and devices.

Various features and advantages of the invention are set forth in the following claims.

What is claimed is:

1. A device for establishing an access channel to a target location, the device comprising:
a plurality of cylindrical segments, each segment having a first end, a second end, a central bore, and a plurality of backbone channels, the first end being convex-shaped relative to the second end;
a plurality of backbones each positioned through one of the plurality of backbone channels of each cylindrical segment to join the plurality of segments together, wherein the first end of one cylindrical segment is at least partially received by the second end of a second cylindrical segment, and wherein, the central bore of each of the plurality of cylindrical segments align to form an access channel; and
a distal segment, wherein each of the plurality of backbones is fixedly attached to the distal segment such that an orientation of the distal segment is adjusted by linear movement of one or more of the plurality of backbones through the plurality of cylindrical segments and when linear movement of the plurality of backbones is restricted the shape of the channel can be adjusted by external forces while maintaining the orientation of the distal segment.

2. The device of claim 1, wherein each of the cylindrical segments includes a wall around the circumference of the central bore, and further comprising a recess in the wall aligned with one of the backbone channels, wherein a backbone extends from the recess between two cylindrical segments.

3. The device of claim 1, further comprising a brace mechanism to couple the device to an inside surface of a structure.

4. The device of claim 3, wherein the brace mechanism includes at least one inflatable balloon, wherein each cylindrical segment includes at least one pneumatic channel, and wherein the at least one inflatable balloon is inflated by air received through the at least one pneumatic channel from a pneumatic pressure source.

5. The device of claim 4, wherein the at least one inflatable balloon of the brace mechanism extends circumferentially around the exterior of the access channel to brace the channel against the inside surface of the structure.

6. The device of claim 3, wherein the brace mechanism includes a plurality of support wires each including a support pad coupled to the distal end of the support wire, and wherein the plurality of support wires extend radially from at least one cylindrical segment.

7. The device of claim 6, wherein each of the plurality of wires includes a flexible preformed wire positioned in a support wire channel of at least one of the cylindrical segments, wherein the support wire channel is arranged substantially parallel to the central bore of the cylindrical segment, and wherein linear movement of the support wire causes the support wire to extend radially from the segment.

8. The device of claim 7, wherein the at least one cylindrical segment includes a recess formed in a circumferential wall of the segment at the first end of the segment, wherein the recess is aligned with the support wire channel such that the support wire extends from the recess.

9. The device of claim 6, wherein each support pad is configured to anchor the access channel with respect to the interior surface of the structure when the support wires are radially extended from the at least one cylindrical segment.

10. The device of claim 1, further comprising a locking mechanism that locks the position of one cylindrical segment relative to another cylindrical segment.

11. The device of claim 10, wherein the locking mechanism includes a rotatable shaft, wherein each cylindrical segment includes a shaft channel and a locking tab biased towards the center of the shaft channel, wherein each locking tab is configured to engage the rotatable shaft when the rotatable shaft is in a first position and to disengage the rotatable shaft when the rotatable shaft is rotated to a second position, and wherein, when the locking tab is engaged with the rotatable shaft, linear movement of the rotatable shaft through the shaft channel is restricted.

12. The device of claim 11, wherein, when the locking tab of a first cylindrical segment and the locking tab of an adjoining cylindrical segment are both engaged with the rotating shaft, angular movement of the first cylindrical segment relative to the adjoining cylindrical segment is restricted.

13. The device of claim 11, wherein, when the locking tab is disengaged from the rotatable shaft, the rotatable shaft is able to move linearly through the shaft channel, and wherein angular movement of the cylindrical segment relative to an adjoining cylindrical segment causes the rotatable shaft to move through the shaft channel.

14. The device of claim 11, wherein the rotatable shaft includes a plurality of teeth on a first side of the rotatable shaft and a smooth surface on a second side of the rotatable shaft, and wherein the bias of the locking tab extends the locking tab between two of the plurality of teeth of the rotating shaft to engage with the rotating shaft when the rotating shaft is positioned with the first side proximate to the locking tab.

15. The device of claim 14, wherein rotating the rotatable shaft so that the second is positioned proximate to the locking tab forces the locking tab to withdraw from the shaft channel causing the locking tab to disengage from the rotatable shaft.

16. The device of claim 1, wherein each backbone includes a super-elastic NiTi wire.

17. The device of claim 1, wherein each backbone includes at least one of a Kevlar strand and stainless steel wire rope with a low bending resistance.

18. A method for establishing an access channel to a target location in an anatomical structure, the method comprising:
inserting a passively flexible device into an orifice of a patient, the passively flexible device including:
a plurality of cylindrical segments, each segment having a first end, a second end, a central bore, and a plurality of backbone channels, the first end being convex shaped relative to the second end,
a plurality of backbones each positioned through one of the plurality of backbone channels of each cylindrical segment to join the plurality of segments together, wherein the first end of one cylindrical segment is at least partially received by the second end of a second cylindrical segment, and wherein, the central bore of each of the plurality of cylindrical segments align to form an access channel, and
a distal segment, wherein each of the plurality of backbones is fixedly attached to the distal segment such that an orientation of the distal segment is adjusted by linear movement of one or more of the plurality of backbones through the plurality of cylindrical segments and when linear movement of the plurality of backbones is restricted the shape of the channel can be adjusted by external forces while maintaining the orientation of the distal segment;

positioning the distal segment of the passively flexible device at the target location; and bracing the passively flexible device to anatomical features at the target location and thereby defining a shape of the flexible device.

19. The method of claim 18, further comprising, moving the distal segment of the flexible device to inspect the deep anatomy while maintaining the shape of the flexible device.

20. The method of claim 18, further comprising passing a tool the target location using the access channel of the flexible device as a guide and thereby protecting the surrounding anatomy.

\* \* \* \* \*